United States Patent [19]
Willis et al.

[11] 4,206,089
[45] Jun. 3, 1980

[54] 5-ALKYLBICYCLO[4.3.0]NON-1-EN-3-ONE AND 5-ALKYLBICYCLO[4.3.0]NONANE-3-ONE PERFUME COMPOSITIONS

[75] Inventors: Brian J. Willis, Bergenfield, N.J.; Robert G. Eilerman, Hempstead, N.Y.

[73] Assignee: Fritzsche Dodge & Olcott Inc., New York, N.Y.

[21] Appl. No.: 888,778

[22] Filed: Mar. 21, 1978

[51] Int. Cl.² .......................... A61K 7/46; C11B 9/00
[52] U.S. Cl. .................... 252/522; 426/534; 434/358; 568/374; 560/122
[58] Field of Search ............... 252/522; 260/586 F

[56] References Cited
U.S. PATENT DOCUMENTS

| | | | |
|---|---|---|---|
| 3,681,464 | 8/1972 | Theimer | 260/586 F |
| 3,703,479 | 11/1972 | Theimer | 252/522 |

*Primary Examiner*—Veronica O'Keefe
*Attorney, Agent, or Firm*—Cooper, Dunham, Clark, Griffin & Moran

[57] ABSTRACT

Novel bicyclic ketones having the structure:

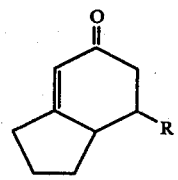

wherein R is a $C_1$–$C_5$ alkyl group, either straight-chain or branched, and saturated analogs have been prepared. These compounds exhibit floral and woody odors and/or desirable flavor properties, and are useful as fragrance and/or flavor materials. The compounds are conveniently prepared from alkylidene cyclopentanones by Michael addition with alkyl metalloacetoacetates and subsequent decarboxylative cyclization of the adducts. The saturated analogs may then be prepared by hydrogenation.

5 Claims, No Drawings

5-ALKYLBICYCLO[4.3.0]NON-1-EN-3-ONE AND 5-ALKYLBICYCLO[4.3.0]NONANE-3-ONE PERFUME COMPOSITIONS

New and distinctive aromatic chemicals, which can be conveniently and inexpensively prepared and readily incorporated into perfume and flavor compositions are in high demand for use in fragrances, cosmetics, foods, spicing compounds, and the like. The present invention concerns the preparation of such compounds and compositions.

Specifically, the present invention provides bicyclic ketones which exhibit aromatic characteristics, such as floral and woody odors, and/or desirable flavor characteristics rendering them valuable as fragrance and/or flavoring materials. The bicyclic ketones are prepared from known alkylidene cyclopentanones by Michael addition with alkyl metallo-acetoacetates and subsequent decarboxylative cyclization of the adducts. The invention also relates to compositions useful as fragrances and/or flavors which contain these bicyclic ketones in an amount sufficient to impart fragrance and/or flavor thereto.

Accordingly, it is a principal object of the invention to provide novel bicyclic ketones.

It is a related object to provide a method of preparing these bicyclic ketones.

Another object of the invention is to provide perfume and/or flavor compositions which contain these bicyclic ketones in an amount sufficient to impart fragrance and/or flavor thereto, or to effectively modify or enhance the fragrance or flavor character of the compositions.

How these and other objects of this invention are achieved will become apparent in the light of the accompanying disclosure. At least one of these objects is accomplished in at least one embodiment of this invention.

DETAILED DESCRIPTION OF THE INVENTION

In accordance with the invention, novel bicyclic ketones having the structure:

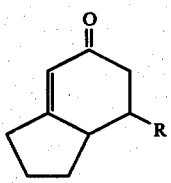

wherein R is an alkyl group, either straight-chain or branched, having from one to five carbon atoms, have been prepared and utilized as fragrance and flavor materials.

It is to be understood in the present disclosure that the compounds of structure I have two asymmetric carbon atoms and can, therefore, exist as a mixture of the two stereoisomeric forms.

The bicyclic ketones of this invention represented by structure I can be prepared by the Michael condensation of an alkylidene cyclopentanone, wherein the alkyl radical contains from one to five carbon atoms, with a lower alkyl acetoacetate in the presence of a condensation catalyst. Subsequent decarboxylative cyclization of the resulting lower alkyl 2-acetyl-3-(2-oxocyclopentyl)alkanoate gives the desired 5-alkylbicyclo [4.3.0] non-1-en-3-one.

The starting material utilized in carrying out the present invention is an alkylidene cyclopentanone having the structure:

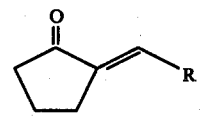

wherein R is as set forth above. Such alkylidene cyclopentanones can be prepared by the method of Birkofer [Chem. Ber., 95, 1495 (1962)] which involves the reaction of a cyclopentanone enamine (e.g. 1-morpholino-1-cyclopentene) with an alkyl aldehyde (e.g. RCHO) with azeotropic removal of water and subsequent hydrolysis of the new enamine so obtained.

The condensation of the appropriate alkylidene cyclopentanone with an alkyl acetoacetate is carried out in the presence of a catalytic quantity of an alkali metal alkoxide. The metallic constituent can be lithium, sodium, or potassium, the preferred metal for use herein being sodium. The condensation is desirably carried out by adding first the alkyl acetoacetate (e.g. methyl acetoacetate) and then the alkylidene cyclopentanone to a solution prepared by dissolving sodium in an excess of an anhydrous alcohol (e.g. methanol) and results in adducts having the structure:

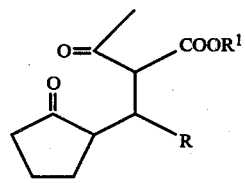

wherein R has the meaning set forth above and $R^1$ represents a lower alkyl group having from one to four carbon atoms. This reaction is conveniently effected at a temperature of from about $-10°$ to $80°$ C., preferably, from about $0°$ to $30°$ C. Although equimolar quantities of reactants may be employed, it is preferred to utilize an excess of the alkyl acetoacetate in this process. Normally, up to about 15 percent molar excess of the acetoacetate is desirable.

The decarboxylative cyclization of the Michael adduct (represented by structure III) may be carried out using any one of the following processes:

i. The substituted acetoacetate can be heated with a mixture of acetic acid and an aqueous mineral acid such as sulfuric acid or hydrochloric acid at reflux for a period of from about 8 to 30 hours.

ii. The adduct can be treated with a 5 percent solution of sodium or potassium hydroxide in alcohol (e.g. methanol or ethanol) at reflux for about 3 to 6 hours.

iii. When $R^1$ is methyl or ethyl (preferably methyl), the bicyclic ketones (represented by structure I) can be obtained by treatment with an alkali metal halide (e.g. chloride, bromide, or iodide) or cyanide in an aprotic solvent such as dimethyl sulfoxide, dimethylformamide, or hexamethylphosphoramide. A preferred method consists of heating the substituted acetoacetate at reflux with a mixture of several equivalents of lithium bromide in dimethylformamide for from about 1 to 4 hours.

iv. When $R^1$ is t-butyl, the process can be accomplished by heating the adduct represented by structure III in a hydrocarbon solvent (e.g. benzene, toluene, or xylene) in the presence of a catalytic amount of p-toluenesulfonic acid.

The bicyclic ketones described hereinabove may be hydrogenated to provide the saturated analogs having the structure:

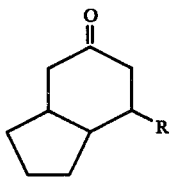

IV wherein R is as set forth above.

The hydrogenation is carried out according to standard methods in the presence of a hydrogenation catalyst (e.g. palladium on carbon). If desirable or necessary, the hydrogenation can be carried out in the presence of an inert solvent such as an alcohol or the like to moderate the hydrogenation.

The hydrogenation is desirably carried out at temperatures of from about 25° to about 50° C. The pressure utilized is desirably from about 1 to 5 atmospheres, and catalyst amounts of from about 1 to 10 percent of the bicyclic ketone are preferred.

The novel bicyclic ketones, both saturated and unsaturated, in which the R group is a straight-chain or branched alkyl group having from one to five carbon atoms produced according to the present invention are preferred for use in imparting fragrances and/or flavors to compositions.

Especially preferred compounds, according to this invention, are those in which R represents a butyl group inasmuch as these compounds have particularly desirable organoleptic properties.

The following examples serve to illustrate the preparation of specific bicyclic ketones in accordance with the invention, but are not meant to limit the scope thereof.

EXAMPLE 1

Pentylidene cyclopentanone (304 g, 2 mol) in dry methanol (250 ml) is added dropwise with stirring over about 3 hours and under nitrogen to a cold (0° C.) solution of methyl sodioacetoacetate [prepared from sodium metal (5.3 g, 0.23 g-atom) and methyl acetoacetate (267 g, 2.3 mol) in dry methanol (700 ml)]. The reaction mixture is stirred at 0° C. for 30 minutes and allowed to stand overnight at room temperature (the reaction can be accelerated by warming the reaction mixture) at which time the formation of the adduct is substantially complete. The adduct is recovered in essentially pure form by adding acetic acid (15 g, 0.25 mol), removing approximately ⅔ of the solvent in vacuo, and pouring the residue into distilled water (1,000 ml) with stirring to induce crystallization of the adduct which is then removed by filtration.

The adduct is mixed with glacial acetic acid (1,500 ml) and 3 N hydrochloric acid (1,500 ml) and is heated at reflux with stirring for 24 hours. The reaction mixture is cooled, the organic layer separated, and the aqueous layer extracted with benzene. The combined organic layers are washed successively with water, saturated sodium bicarbonate, and brine followed by drying over sodium sulfate. The benzene is removed under partial vacuum and the crude bicyclic ketone distilled through a 12"×1" column packed with Raschig rings (6×6 mm) to give 250 g (bp 101°–107° C. at 0.5 mm) of 5-butylbicyclo [4.3.0] non-1-en-3-one which can be represented by the structure:

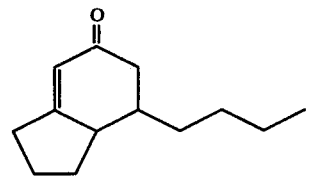

EXAMPLE 2

Pentylidene cyclopentanone (200 g, 1.3 mol) in dry ethanol (200 ml) is added dropwise over 2 hours at 0°–5° C. to a solution of ethyl sodioacetoacetate prepared from sodium metal (3.5 g, 0.15 mol) and ethyl acetoacetate (196 g, 1.5 mol) in ethanol (500 ml). The mixture is allowed to slowly warm to room temperature and stirred overnight. The adduct is recovered by neutralizing the solution with acetic acid (9 g) and removing the ethanol by rotary evaporation.

The crude adduct is mixed with glacial acetic acid (1,000 ml) and 3 N hydrochloric acid (1,200 ml) and heated at reflux overnight (20 hours). The cooled reaction mixture is extracted with benzene and the combined extracts are washed with water, saturated sodium bicarbonate solution, and brine followed by drying over sodium sulfate. The benzene is removed and the crude ketone fractionated through a 12" Vigreaux column to yield 167 g of 5-butylbicyclo [4.3.0] non-1-en-3-one having bp 100°–106° C. at 0.5 mm.

EXAMPLE 3

The procedure of Example 1 is repeated with 85 g (0.56 mol) of isopentylidene cyclopentanone, 1.61 g (0.07 g-atom) of sodium, 76.5 g (0.66 mol) of methyl acetoacetate and 300 ml of methanol. Upon distillation there are obtained 56 g (bp 97°–100° C. at 0.5 mm) of 5-isobutylbicyclo [4.3.0] non-1-en-3-one having the structure:

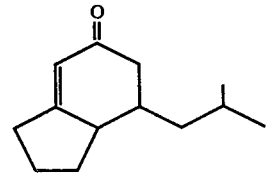

EXAMPLE 4

The procedure of Example 1 is repeated with 19.5 g (0.16 mol) of propylidene cyclopentanone, 0.46 g (0.02 g-atom) of sodium, 21 g (0.18 mol) of methyl acetoacetate and 100 ml of methanol. Fractional distillation yields 14 g (bp 95°–102° C. at 0.5 mm) of 5-ethylbicyclo [4.3.0.] non-1-en-3-one having the structure:

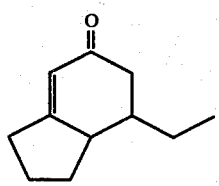

EXAMPLE 5

The procedure of Example 1 is repeated with 98.5 g (0.59 mol) of hexylidene cyclopentanone, 1.61 g (0.072 g-atom) of sodium, 82 g (0.71 mol) of methyl acetoacetate, and 300 ml of methanol. The crude product is fractionated giving 70 g (bp 117°–123° C. at 0.5 mm) of 5-pentylbicyclo [4.3.0] non-1-en-3-one having the structure:

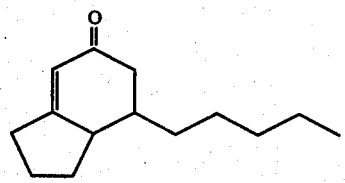

EXAMPLE 6

Methyl 2-acetyl-3-(2-oxocyclopentyl) heptanoate (13.4 g, 0.05 mol), which is prepared according to the first part of the procedure of Example 1, is mixed with 40 ml of methanol containing potassium hydroxide (1.7 g) and heated at reflux under nitrogen for 4 hours. The reaction mixture is cooled and added to 150 ml of dilute aqueous hydrochloric acid and extracted three times with benzene. After washing with water and brine, the extract is dried over sodium sulfate and the benzene removed on a rotary evaporator. Distillation gives 7.2 g (bp 100°–105° C. at 0.5 mm) of 5-butylbicyclo [4.3.0] non-1-en-3-one.

EXAMPLE 7

Vacuum-dried methyl 2-acetyl-3-(2-oxocyclopentyl) heptanoate (16.1 g, 0.06 mol), which is prepared according to the first part of the procedure of Example 1, and dry lithium bromide (17 g, 0.19 mol) are mixed in 45 ml of dry dimethylformamide and heated at reflux in a nitrogen atmosphere. After 2 hours no starting material remains and the reaction mixture is cooled to room temperature. It is poured into 300 ml of water and extracted with ether. The ether extract is washed with water, dried over sodium sulfate, and the ether evaporated. Distillation gives 10 g (bp 102°–106° C. at 0.5 mm) of pure 5-butylbicyclo [4.3.0] non-1-en-3-one.

EXAMPLE 8

5-Butylbicyclo [4.3.0] non-1-en-3-one (120 g) is hydrogenated in ethyl acetate (125 ml) over 1.5 g of 5% palladium on carbon at a pressure of 4 atmospheres in a Parr apparatus. The solution is filtered through celite to remove the catalyst, concentrated, and the residue is vacuum distilled through a 12" Vigreaux column to yield 114 g (bp 98°–102° C. at 0.5 mm) of 5-butylbicyclo [4.3.0] nonan-3-one represented by the structure:

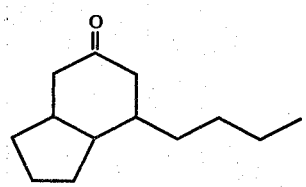

EXAMPLE 9

5-Isobutylbicyclo [4.3.0] non-1-en-3-one (25.4 g, 0.13 mol) is treated according to the procedure of Example 8 with 0.5 g of 5% palladium on carbon. Distillation gives 24 g (bp 90°–92° C. at 0.5 mm) of pure 5-isobutylbicyclo [4.3.0] nonan-3-one represented by the structure:

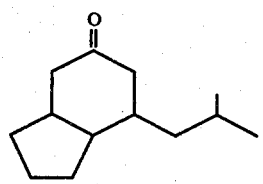

The bicyclic ketones of this invention, as previously disclosed herein, are useful as fragrance and/or flavor materials. Accordingly, one or a combination of these compounds are useful in the preparation of perfumes and fragrances or fragrant compositions or are usefully incorporated in other composition to impart a desirable aroma or fragrance thereto.

When employed in perfumes or fragrant compositions or when employed in flavor compositions to impart a desired fragrance, aroma, or flavor character thereto, the compounds of this invention are incorporated therein in an amount sufficient to impart a desired aromatic character thereto, such as an amount in the range from about 0.001 to about 50% by weight, usually an amount in the range 0.1 to about 20% by weight.

Formulations of fragrances employing a compound in accordance with this invention are set forth hereinafter. Table I shows the makeup of a jasmin fragrance employing the compound 5-butylbicyclo [4.3.0] non-1-en-3-one. Table II illustrates the make-up of an oriental chypre fragrance employing the compound 5-butylbicyclo [4.3.0] nonan-3-one. Table III shows the make-up of a tuberose fragrance employing the compound 5-isobutylbicyclo [4.3.0] non-1-ene-3-one.

TABLE I

| % Wt. | Component | Jasmin |
|---|---|---|
| 0.5 | Indole | |
| 2.0 | Eugenol | |
| 2.0 | Benzyl salicylate | |
| 20.0 | Amyl cinnamic aldehyde | |
| 2.5 | n-Hexylbenzoate | |
| 2.0 | Methyl anthranilate 10% | Sol. in DEP |
| 2.0 | Terpineol | |
| 2.0 | Nerol | |
| 8.0 | Linalool | |
| 1.0 | Cis 3-hexenol 10% | Sol. in DEP |
| 1.0 | Gamma undecalactone 10% | Sol. in DEP |
| 0.5 | Benzoin resinoid | |
| 1.0 | Phenyl ethyl alcohol | |
| 0.5 | Dimethyl benzylcarbinylacetate | |
| 20.0 | Benzyl alcohol | |
| 20.0 | Benzyl acetate | |
| 4.0 | 5-Butylbicyclo [4.3.0] non-1-en-3-one | |

TABLE I-continued

Jasmin

| % Wt. | Component |
|---|---|
| 100.0 | |

TABLE II

Oriental Chypre

| % Wt. | Component | % Wt. | Component |
|---|---|---|---|
| 8.0 | Vanillin | 0.5 | Rose oil Bulgarian |
| 4.0 | Musk ketone | 0.5 | Jasmin absolute |
| 2.0 | Oakmoss absolute | 6.0 | Oil Ylang Ylank extra |
| 2.0 | Methyl ionone gamma | 0.5 | Oil Estragon |
| 1.0 | Isoamyl salicylate | 1.0 | Oil Coriander |
| 8.0 | Oil Vetiver Reunion | 4.0 | Oil Neroli synthetic |
| 4.0 | Hydroxycitronellal | 2.0 | Benzoin resinoid |
| 1.0 | Eugenol | 4.0 | Oil Petitgrain |
| 2.0 | Phenyl ethyl alcohol | 4.0 | Oil Lemon Haitian |
| 2.0 | Rhodinol | 12.0 | Oil Patchouly |
| 8.0 | Linalool | 4.0 | Benzyl acetate |
| 4.0 | Linalyl acetate | 12.0 | Oil Bergamot Rect. |
| 1.0 | Labdanum absolute | 2.0 | 5-Butylbicyclo [4.3.0] nonan-3-one |
| 0.5 | Styrax oil | | |
| | | 100.0 | |

TABLE III

Tuberose

| % Wt. | Component |
|---|---|
| 2.5 | Tolu resinoid |
| 10.0 | Benzyl salicylate |
| 30.0 | Hydroxycitronellal |
| 10.0 | Methyl anthranilate |
| 10.0 | Linalool synthetic |
| 10.0 | Geraniol |
| 5.0 | Ylang Ylang absolute |
| 5.0 | Methyl benzoate |
| 5.0 | Benzyl acetate |
| 2.5 | Gamma nonalactone |
| 0.5 | Gamma undecalactone |
| 0.5 | Methyl heptine carbonate |
| 2.0 | Eugenol |
| 2.0 | Methyl salicylate |
| 5.0 | 5-Isobutylbicyclo [4.3.0] non-1-en-3-one |
| 100.0 | |

The bicyclic ketones of this invention may be employed for flavoring, as such, or as part of a mixture of other flavor components.

When employed in flavor compositions or when added to other compositions, such as foodstuffs, e.g. sausages, salad dressings and soup, the compounds of this invention are incorporated therein in an amount effective to impart desired flavor thereto, such as an amount in the range of about 0.0001 to about 40% by weight, usually in an amount of 0.001 to about 20% by weight.

One of the bicyclic ketones of this invention, namely, 5-butylbicyclo [4.3.0] non-1-en-3-one, is particularly useful to impart a celery flavor character. At concentrations above about 1 ppm it imparts a celery-like flavor and aroma to foodstuffs in which it is incorporated.

As will be apparent to those skilled in the art in light of the foregoing disclosure, many modifications, alterations and substitutions are possible in the practice of this invention without departing from the spirit or scope thereof.

We claim:

1. A fragrance composition which comprises an effective fragrance-imparting amount of one or more compound having the structure:

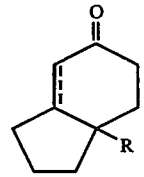

wherein R is a $C_1$–$C_5$ alkyl group and wherein the dashed line may represent a carbon-carbon double bond or a carbon-carbon single bond in combination with conventional fragrance ingredients.

2. A fragrance composition in accordance with claim 1 wherein said effective fragrance-imparting amount is an amount in the range of from about 0.0001 to about 50% by weight based upon the weight of said composition.

3. A fragrance composition in accordance with claim 1 wherein the dashed line represents a carbon-carbon double bond.

4. A fragrance composition in accordance with claim 1 wherein the dashed line represents a carbon-carbon single bond.

5. A fragrance composition in accordance with claim 1 wherein R is n-butyl.

* * * * *

UNITED STATES PATENT AND TRADEMARK OFFICE
CERTIFICATE OF CORRECTION

PATENT NO. : 4,206,089
DATED : June 3, 1980
INVENTOR(S) : Brian J. Willis and Robert G. Eilerman It is certified that error appears in the above-identified patent and that said Letters Patent are hereby corrected as shown below:

Column 8, Claim 1, line 25, the structure should read:

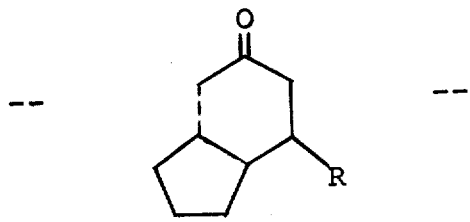

Column 6, line 50, "non-1-ene-3-one" should read

-- non-1-en-3-one --.

Table II, Col. 7, line 13, "Oil Ylang Ylank extra" should read

-- Oil Ylang Ylang extra --.

Signed and Sealed this

Fifth Day of August 1980

[SEAL]

Attest:

SIDNEY A. DIAMOND

Attesting Officer

Commissioner of Patents and Trademarks